(12) United States Patent
Stephens et al.

(10) Patent No.: US 11,872,711 B2
(45) Date of Patent: Jan. 16, 2024

(54) LUBRICATING MEMBER FOR RAZOR CARTRIDGES

(71) Applicant: The Gillette Company LLC, Boston, MA (US)

(72) Inventors: Alison Fiona Stephens, Maidenhead (GB); Joia Kirin Spooner-Fleming, Jamaica Plain, MA (US)

(73) Assignee: The Gillette Company LLC, Boston, MA (US)

( * ) Notice: Subject to any disclaimer, the term of this patent is extended or adjusted under 35 U.S.C. 154(b) by 648 days.

(21) Appl. No.: 16/864,198

(22) Filed: May 1, 2020

(65) Prior Publication Data

US 2020/0353634 A1 Nov. 12, 2020

Related U.S. Application Data

(60) Provisional application No. 62/846,224, filed on May 10, 2019.

(51) Int. Cl.

| | |
|---|---|
| *B26B 21/44* | (2006.01) |
| *A61K 8/34* | (2006.01) |
| *A61K 8/73* | (2006.01) |
| *A61K 8/86* | (2006.01) |
| *A61K 8/894* | (2006.01) |
| *A61K 8/92* | (2006.01) |
| *A61Q 9/02* | (2006.01) |

(52) U.S. Cl.
CPC ............ *B26B 21/443* (2013.01); *A61K 8/342* (2013.01); *A61K 8/731* (2013.01); *A61K 8/86* (2013.01); *A61K 8/894* (2013.01); *A61K 8/92* (2013.01); *A61Q 9/02* (2013.01); *A61K 2800/87* (2013.01)

(58) Field of Classification Search
CPC ................................ B26B 21/443; A61Q 9/02
See application file for complete search history.

(56) References Cited

U.S. PATENT DOCUMENTS

| | | | |
|---|---|---|---|
| 2,838,442 A | 6/1958 | Mcmaster | |
| 5,113,585 A | 5/1992 | Rogers | |
| 5,349,750 A | 9/1994 | Tseng | |
| 6,161,288 A | 12/2000 | Andrews | |
| 6,298,558 B1 | 10/2001 | Tseng | |
| 6,301,785 B1 | 10/2001 | Kwiecien et al. | |
| 6,449,849 B1 | 9/2002 | Hackerman | |
| 7,024,776 B2 | 4/2006 | Wain | |
| 7,197,825 B2 | 4/2007 | Walker et al. | |
| 7,607,230 B2 | 10/2009 | Aviza et al. | |
| 8,236,214 B2 | 8/2012 | Kwiecien | |
| 9,119,796 B2 | 9/2015 | Cook et al. | |
| 9,216,514 B2 | 12/2015 | Bridges et al. | |
| 10,675,772 B2 | 6/2020 | Fontecchio et al. | |
| 10,682,778 B2 | 6/2020 | Hayes et al. | |
| 2006/0018968 A1 | 1/2006 | Melbouci | |
| 2006/0035861 A1 | 2/2006 | Berg et al. | |
| 2008/0034590 A1 | 2/2008 | Prudden, Jr. et al. | |
| 2008/0060201 A1 | 3/2008 | Kwiecien | |
| 2008/0254209 A1 | 10/2008 | Dorgan | |
| 2009/0049695 A1 | 2/2009 | Keene et al. | |
| 2011/0041865 A1 | 2/2011 | Stephens et al. | |
| 2012/0023763 A1 | 2/2012 | Ariyanayagam et al. | |
| 2012/0087981 A1* | 4/2012 | Wang .................. | A61K 8/86 514/159 |
| 2012/0097981 A1 | 4/2012 | Chang | |
| 2013/0042482 A1 | 2/2013 | Bradford et al. | |
| 2014/0366381 A1 | 12/2014 | Phipps et al. | |
| 2016/0199990 A1 | 7/2016 | Nicholas et al. | |
| 2017/0000721 A1* | 1/2017 | Bradford ............... | B26B 21/443 |
| 2017/0334082 A1 | 11/2017 | Hayes et al. | |
| 2018/0117780 A1 | 5/2018 | Moloney et al. | |
| 2022/0202677 A1 | 6/2022 | Stephens et al. | |

FOREIGN PATENT DOCUMENTS

| | | |
|---|---|---|
| CN | 104498551 A | 4/2015 |
| EP | 1630525 A2 | 3/2006 |
| JP | 2013139422 | 7/2013 |
| WO | 2013111979 A1 | 8/2013 |

OTHER PUBLICATIONS

Cekol 30000 P (https://www.signetexcipients.com/Content/Upload/949Xt9Cekol30000PPDS.pdf) available Sep. 22, 2009, pp. 1-2. (Year: 2009).*
International Search Report and Written Opinion; Application Ser. No. PCT/US2020/032300; dated Aug. 13, 2020; 14 pages.
All Office Actions; U.S. Appl. No. 17/551,982, filed Dec. 15, 2021.
All Office Actions; U.S. Appl. No. 17/944,839, filed Sep. 14, 2022.
Choi et al., "Promotion Effects of Ultra-High Molecular Weight Poly-y-Glutamic Acid on Wound Healing", Journal of Microbiology and Biotechnology, vol. 25, No. 6, Mar. 20, 2015, pp. 941-945.
Lee et al., "In vitro evaluation of new functional properties of poly-y-glutamic acid produced by Bacillus Subtilis D7", Saudi Journal of Biological Science, vol. 21, Sep. 17, 2013, pp. 153-158.
U.S. Appl. No. 17/944,839, filed Sep. 14, 2022, to Alexander Shih Lee et. al.

* cited by examiner

*Primary Examiner* — Andrew S Rosenthal
(74) *Attorney, Agent, or Firm* — Kevin C. Johnson

(57) ABSTRACT

The invention relates to a lubricating member for a razor cartridge having a lubricating member comprising a carboxymethyl cellulose.

19 Claims, No Drawings

LUBRICATING MEMBER FOR RAZOR CARTRIDGES

BACKGROUND OF THE INVENTION

The use of shaving aids on razor blades to provide lubrication benefits during the shave is known, see for example U.S. Pat. Nos. 7,121,754, 6,298,558, 5,711,076, 5,134,775, 6,301,785, U.S. 2009/0223057, US 2006/0225285US2016/0143836A1, US2018/0133139A1, and US2017/0002288A1. Such shaving aids typically comprise a water-insoluble matrix material to provide structural integrity and a water-soluble polymer, such as polyethylene oxide (polyox), in order to provide lubrication during the shave once the water-soluble polymer forms a solution with the water present during shaving. Since the introduction of polyox as a shaving lubricant, little development has been made in the field, even though polyethylene oxide polymers are not without limitations.

For example, utilizing polyethylene oxide polymers having low molecular weights or high molecular weights may improve lubrication, but may also result in trade off with regard to residue and or stringiness or other aspects of the aqueous solution typically formed in-use. It is believed that the resultant viscosity in aqueous solution may also increase, leading to negatively perceived attributes, for example concerning the feeling of the shave for the user, particularly in respect of the lubricant. Combinations of high and low molecular weight polyethylene oxide polymers in order to balance these performance attributes has also been described. Nevertheless, such combinations are also limited in their ability to improve performance and or suffer from other negative performance attributes.

The addition of certain cellulose materials into a shaving aid are known, including hydroxypropyl cellulose ("HPC") and hydroxethyl cellulose ("HEC"). See e.g. U.S. Pat. No. 5,113,585. HPC and HEC are thermoplastic in nature, meaning they are solids at standard environmental conditions and will soften/melt as exposed to higher temperatures. When used in current lubricating member extrusion processing conditions, the HPC/HEC components will form part of the molten phase with any polyethylene oxide during extrusion. One problem with using thermoplastic celluloses is that they can alter the melt viscocity of the lubricating member during the extrusion step. This can be particularly problematic as the molecular weight of the thermoplastic cellulose increases. As such, there is a desire to find certain polymers that can provide in proved lubrication but avoid the issues encountered with thermoplastic celluloses.

Carboxymethyl cellulose ("CMC") is another type of cellulosic material that has been disclosed for use in a shaving context. CMC is not thermoplastic and does not melt under traditional extrusion temperatures (which can be as high as 150° C., as high as 180 or 200° C.). For example, U.S. Pat. No. 2,838,442 describes a solid shaving stick block comprising carboxymethyl cellulose but does not contain polyethylene oxide. US2012/0087981A1 discloses shaving aids for use on the razor to deliver lubrication and encapsulated fragrances where CMC can be used as the capsule material. Despite these specific uses of CMC in shaving applications, there remains a need to find ways to improve lubrication while avoiding one or more of the issues with known applications of cellulose materials in the art.

SUMMARY OF THE INVENTION

One aspect of the present invention relates to a razor comprising: a housing having a lubricating surface; at least one blade with a blade tip, wherein said blade tip is exposed on said lubricating surface of the housing; a lubricating member position on the lubricating surface of said housing, said lubricating member comprising a lubricating material comprising a mixture of a polyethylene oxide and a carboxymethyl cellulose, wherein said carboxymethyl cellulose forms at least one discreet particle. The carboxymethyl cellulose may have a formulas of:

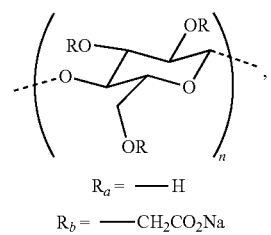

$R_a =$ ——H
$R_b =$ ——$CH_2CO_2Na$ wherein the cellulose has 3 R groups per repeating unit, said R groups selected from Ra or Rb.

Another aspect of the present invention relates to a hair removal device comprising: a housing having a lubricating surface; a lubricating member positioned on the lubricating surface of said housing, said lubricating member comprising from about 10% to about 70% of a water soluble polymer comprising polyethylene oxide; from about 5% to 30% of a carboxymethyl cellulose, wherein said carboxymethyl cellulose forms at least one discreet particle.

Alternatively, the lubricating member may comprise more than about 20%, more than about 30% more than about 40% or more than about 50% of a water-soluble polymer comprising polyethylene oxide. The lubricating member may comprise less than about 70%, less than about 60% less than about 50% or less than about 40% of a water-soluble polymer comprising polyethylene oxide. The lubricating member may comprise more than about 20%, more than about 30% more than about 40% or more than about 50% of a carboxymethyl cellulose, wherein said carboxymethyl cellulose forms at least one discreet particle. The lubricating member may comprise less than about 70%, less than about 60% less than about 50% or less than about 40% of a carboxymethyl cellulose, wherein said carboxymethyl cellulose forms at least one discreet particle.

The water-soluble polymer comprising polyethylene oxide and the carboxymethyl cellulose may be present in the lubricating member in a ratio of 1:1 or in a ratio of greater than 1:1 with the carboxymethyl cellulose being the more prevalent component. For example the ratio of carboxymethyl cellulose to water-soluble polymer may be 60:40 or 70:30.

Yet another aspect provides for a lubricating member comprising a water-soluble polymer comprising polyethylene oxide and a particulate carboxymethyl cellulose and a carrier wherein the water-soluble polymer and the carboxymethyl cellulose are dispersed within the carrier material. The carrier material may be a non-water-soluble polymer. The non-water-soluble polymer may comprise high-impact polystyrene (HIPS) or ethylene-vinyl acetate (EVA) or any other suitable non-water-soluble polymer.

Alternately, the carrier may further comprise a mixture of non-water-soluble waxes and oils suitable for use in lubricating members. Non-limiting examples of suitable non-water soluble waxes and oils include those disclosed in U.S. Patent Publication Application No. 2017/0002287 and 2017/0002289. In one embodiment, the lubricating member comprises: a) a lipid phase comprising from about 10% to about 70% by weight of a lipophilic structurant (such as cetyl alcohol, stearyl alcohol, or mixture thereof, or a microcrystalline wax); from about 10% to about 70% by weight of a liquid phase comprising a silicone polyether block polymer; b) PEO; and c) CMC. The PEO can be as low as 10%, such as from about 10% to about 30% by weight. The CMC can be from 10% to about 30%, preferably on the higher range of from about 20% to about 30%. The liquid phase can further comprise a variety of oils and fats, such as natural oil, synthetic oil, natural butter, triglycerides, petrolatum, silicone and mixtures thereof. The silicone polyether block copolymer comprises: a mixture of polyethylene oxide, polypropylene oxide, and silicone (such as in a ratio of units of 20:65:15, and preferably having a molecular weight of from about 10000 to about 19000).

Yet another aspect provides for a method of forming a lubricating member for use on a hair removal device, the method comprising: providing a polyethylene oxide; providing a carboxymethyl cellulose in a solid form; contacting said polyethylene oxide with said carboxymethyl cellulose to form a mixture; forming a lubricating member from said mixture, wherein said carboxymethyl cellulose forms a discreet particle within said lubricating member. Notably, the lubricating member may be formed by molding or casting and not necessarily extrusion.

DETAILED DESCRIPTION OF THE INVENTION

Water Soluble Polymer

According to the present invention, the lubricating member comprises a lubricating material comprising from about 1% to about 99% by weight of water soluble polymer, preferably at least about 15%, more preferably at least about 20%, most preferably at least about 25%, and up to about 70%, preferably up to about 60% by weight of the lubricating member.

The water soluble polymer may comprise a polyethylene oxide (PEO). Examples of other additional suitable water-soluble polymers include, polyvinyl pyrrolidone, polyacrylamide, polyhydroxymethacrylate, polyvinyl imidazoline, polyethylene glycol, polyvinyl alcohol, polyhydroxyethymethacrylate, and mixtures thereof.

The preferred water soluble polymers are the polyethylene oxides generally known as POLYOX (available from Union Carbide Corporation) or ALKOX (available from Meisei Chemical Works, Kyoto, Japan). The water-soluble polymer(s), (especially these polyethylene oxides), may have average molecular weights of at least about 20,000, preferably at least about 50,000, more preferably at least about 100,000 or from about 100,000 to about 8 million, preferably about 300,000 to about 8 million, more preferably from about 1 million to about 5 million, even more preferably about 2 million. A particularly preferred polyethylene oxide comprises a blend of about 40% to 80% of polyethylene oxide having an average molecular weight of about 5 million (e.g. POLYOX COAGULANT) and about 60% to 20% of polyethylene oxide having an average molecular weight of about 300,000 (e.g. POLYOX WSR-N-750). The polyethylene oxide blend may also advantageously contain up to about 10% (for example about 5%) by weight of a low molecular weight (i.e. MW<10,000) polyethylene glycol such as PEG-100.

Carboxymethyl Cellulose

According to the present invention, the lubricating member comprises a carboxymethyl cellulose (CMC). CMC can be included a varying levels, for example from about 5% to about 30%, preferably from about 10% to about 20%, by weight of the lubricating member. In one embodiment, where the lubricating member comprises a lipid phase (as discussed briefly in the Summary), the amount of CMC can be on the higher range, such as from 20% to about 30% by weight of the lubricating member, and the amount of PEO can therefore be lowered such as in the 10% to 30 range. In embodiments such as extruded lubricating members comprising PEO and a non-water soluble polymer (non limiting examples include high impact polystyrene or ethylene vinyl acetate), the level of CMC can be on the lower range, such as from about 5% to about 20%.

One embodiment of the present invention relates to a lubricating member for a razor cartridge comprising PEO and CMC, and further from about 20% to about 90% by weight of a lipid phase, said lipid phase comprising: from about 10% to about 70% by weight of the lubricating member of a lipophilic structurant. Non-limiting examples of suitable lipophilic structurants include cetyl alcohol, stearyl alcohol, or mixture thereof, or a microcrystalline wax. The lipid phase further comprises from about 10% to about 70% by weight of the lubricating member of a liquid phase, wherein said liquid phase comprises a silicone polyether block copolymer comprising a blend of polyethylene oxide, polypropylene oxide and silicone. Nonlimiting examples of suitable silicone polyether block copolymers include: a ratio of polyethylene oxide units to polypropylene oxide units to silicone units of 20:65:15, and a molecular weight of from about 10000 to about 19000. In one embodiment, said lubricating member is substantially free of lathering soap or lathering surfactant.

Suitable carboxymethyl cellulose has a structure according to the formula:

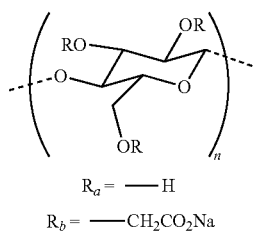

$R_a = \text{———} H$ $R_b = \text{———} CH_2CO_2Na$

Cellulose has three groups (R) available for substitution per repeating unit. For carboxymethyl cellulose, each R group will comprise either $R_a$ or $R_b$ with the 'degree of substitution' being defined as the average number of R groups per repeating cellulose unit that comprise $R_b$. The $R_b$ moiety is the carboxymethyl substituent. The carboxymethyl cellulose has an average degree of carboxymethyl substitution of from 0.6 to 0.9, preferably from 0.7 and preferably to 0.8.

Without intending to be bound by theory, it is believed that the Na+ can be replaced by a hydrogen atom which can happen in situ by reducing compositional pH.

It may be preferred for the carboxymethyl cellulose to be further substituted with a hydrophobic moiety according to the following structure to give a hydrophobically modified carboxymethyl cellulose:

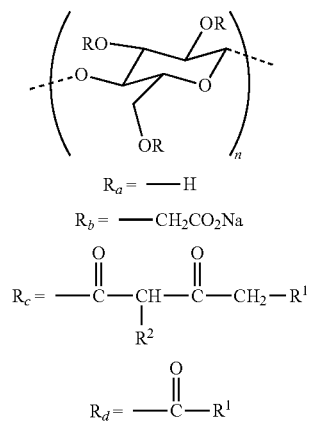

wherein, each R group will comprise either $R_a$, $R_b$, $R_c$, or $R_d$ in which $R^1$ and $R^2$ are independently selected from alkyl or alkenyl chains having from 5 to 22 carbon atoms. The $R_b$ moiety is the carboxymethyl substituent. The $R_c$ and $R_d$ moieties are the hydrophobic substituents. The 'degree of carboxymethyl substitution' is defined as the average number of R groups per repeating cellulose unit that comprise $R_b$. The carboxymethyl cellulose has an average degree of carboxymethyl substitution of from 0.6 to 0.9, preferably from 0.7 and preferably to 0.8. The 'degree of hydrophobic moiety substitution' is defined as the average total number of R groups per repeating cellulose unit that comprise $R_c$, and/or $R_d$. Preferably, the average degree of hydrophobic moiety substitution is in the range of from 0.001 to 0.2.

A typical method to determine the degree of substitution (DS) of carboxymethyl cellulose (CMC) is described in more detail below. A typical method to determine the degree of blockiness (DB) of carboxymethyl cellulose (CMC) is described in more detail below.

CMC suitable for use in this invention can include celluloses including cellulose gums from CP Kelco, including but not limited to Cekol, including Cekol 30000P with typical particle size >0.75 mm, maximum at 20%, and less than 0.25 mm, maximum at 0.5%. The CMC can be granulated or micro grinded. In one embodiment, the CMC to be used in this invention can come from a feed having a CMC particle size of from about 75 microns to about 425 microns, with an average particle size of 100 microns to about 175 microns. In one embodiment, the micro grinded CMC has almost all or all of the CMC with a particle size below 100 microns, and at least 70% less than 50 microns.

Additional suitable types of CMC include some CMCs manufactured by Ashland under their Blanose and Aqualon offerings. Non limiting examples include: Ashland Blanose 9H4F with viscosity of 2500-4000 mPa·s and degree substitution is—0.8-0.95, and Ashland Aqualon 7HF PH with viscosity of 1500-3000 mPa·s and degree substitution of 0.7. It is believed both of these materials are likely to at or below 40,000 MW.

Synthesis of the Carboxymethyl Cellulose

Methods of producing carboxymethyl cellulose are well described in the art and have been disclosed, for example in T. G. Majewicz and T. J. Podlas, Kirk-Othmer's Encyclopedia of Chemical Technology, 4$^{th}$ edition, Chapter 'Cellulose Ethers', Volume 5, pp 445-465.

Methods for controlling 'blockiness' are disclosed in V. Stigsson et al., Cellulose, 2006, 13, pp. 705-712.

Various methods of producing hydrophobically modified carboxymethyl cellulose are disclosed in EP998498 (C. P. Kelco); I. Sroková, V. Tomanová, A. Ebringerová, A. Malovíková, and T. Heinze, Macromolecular Materials and Engineering, 2004, 289 (1), pp. 63-69; and I. Sroková, P. Talába, P. Hodul, and A. Balázová, Tenside, Surfactants, Detergents, 1998, 35 (5), pp. 342-344.

Method to Determine Degree of Carboxymethyl Substitution (DS) of a Carboxymethyl Cellulose (CMC)

The DS was determined by igniting CMC to ash at high temperature (650° C.) for 45 minutes in order to remove all the organic material. The remaining inorganic ashes were dissolved in distilled water and methyl red added. The sample was titrated with 0.1M hydrochloric acid until the solution turned pink. The DS was calculated from the amount of titrated acid (b ml) and the amount of CMC (G g) using the formula below.

$$DS=0.162*\{(0.1*b/G)/[1-(0.08*0.1*(b/G)]\}$$

Alternatively, the DS of a substituted cellulose may be measured by conductimetry or $^{13}C$ NMR. Experimental protocols for both approaches are given in D. Capitani et al, Carbohydrate Polymers, 2000, v42, pp 283-286.

Method to Determine Degree of Blockiness (DB) of a Carboxymethyl Cellulose (CMC)

In the case of a substituted cellulose, the DB may correspond to the amount (A) of non-substituted glucose units released after a specific enzymatic hydrolysis with the commercial endoglucanase enzyme (Econase C E, AB Enzymes, Darmstadt, Germany) divided by the total amount of non-substituted glucose units released after acid hydrolysis (A+B). The enzymatic activity is specific to non-substituted glucose units in the polymer chain that are directly bounded to another non-substituted glucose unit. Further explanation of substituted cellulose blockiness and measurement is provided in detail in V. Stigsson et al., Cellulose, 2006, 13, pp 705-'712.

The enzymatic degradation is performed using the enzyme (Econase CE) in a buffer at pH 4.8 at 50° C. for 3 days. To 25 ml of substituted cellulose sample, 250 µL of enzyme is used. The degradation is stopped by heating the samples to 90° C. and keeping them hot for 15 minutes. The acid hydrolysis for both substitution pattern and blockiness is carried out in perchloric acid (15 min in 70% HClO4 at room temperature and 3 hours in 6.4% HClO4 at 120° C.). The samples are analyzed using Anion Exchange Chromatography with Pulsed Amperiometric Detection (PAD detector: BioLC50 (Dionex, Sunnyvale, California, USA)). The HPAEC/PAD system is calibrated with $^{13}C$ NMR. The monosaccharides are separated at 35° C. using a flow rate of 0.2 ml/min on a PA-1 analytical column using 100 mM NaOH as eluent with increasing sodium acetate (from 0 to 1M sodium acetate in 30 mins). Each sample is analyzed three to five times and an average is calculated. The number of unsubstituted glucose that were directly linked to at least one substituted glucose (A), and the number of unsubstituted glucose that were not directly linked to a substituted glucose (B) are deduced and the DB of the substituted cellulose sample is calculated: DB=B/(A+B).

Method to Determine Degree of Hydrophobic Moiety Substitution of a Hydrophobically Modified Carboxymethyl Cellulose (CMC)

The degree of hydrophobically moiety substitution is determine using FT-IR spectroscopy as described in I. Sroková, V. Tomanová, A. Ebringerová, A. Malovíková, and T. Heinze, Macromolecular Materials and Engineering, 2004, 289 (1), pp. 63-69; and I. Sroková, P. Talába, P. Hodul, and A. Balázová, Tenside, Surfactants, Detergents, 1998, 35 (5), pp. 342-344.

Lubricating Member Comprising PEO and CMC

The invention comprises a lubricating member comprising a mixture of PEO and CMC. The lubricating member forms a matrix of material wherein the CMC forms at least one, preferably a plurality of discreet particles within said matrix. In some embodiments the matrix can comprise the PEO alone, PEO with other optional lubricants or other ingredients including but not limited to ingredients that comprise the carrier such as non-water-soluble polymers, non-water-soluble and/or hydrophobic waxes and oils, hydrophobic binders, and the like.

The CMC forms at least one discreet particle having a particle diameter less than 600 microns, less than about 425 microns, less than about 250 microns, or less than 100 microns. In an alternate embodiment, said plurality of carboxymethyl cellulose particles has an average particle size of less than about 600 microns, preferably less than about 400 microns, preferably less than about 300 microns. In one embodiment, the average particle size can be as low as 100 microns, or even lower.

In one embodiment at least 10% of the CMC, by weight, forms said discreet particles, preferably at least 25%, preferably at least 50%. It can be desired that even higher amounts of the CMC form said discreet particles, as high as 90%, 95%, or even about 99% up to 100% of the CMC.

In one embodiment, the lubricating member has a ratio of CMC to water soluble polymer in the range of 1:1 to about 7:3, most preferably 55:45 to 65:35.

Without being bound by theory it is believed that the CMC enables a more viscous lubricating solution and layer under the cartridge which is beneficial to the consumer. As CMC is not as visco elastic as PEO it does this whilst also decreasing the negative consumer attribute of stringiness and residue. Net it is believed that a lubricating member comprising both PEO and CMC improves lubrication, a feeling of protection whilst decreasing negative signals on the skin.

Optional Silicone Polyether Copolymer

According to one embodiment of the invention, the lubricating material further comprise from about 0.1% to about 70%, preferably from about 1% to about 20%, more preferably from about 1% to 15%, even more preferably from about 1% to about 5% or alternatively from about 40% to about 60%, more preferably from about 45% to about 55%, by weight of a silicone polyether copolymer or mixtures thereof.

The silicone polyether copolymer comprises from about 1% to 50%, by weight of polyethylene oxide, from about 20% to about 90% by weight of polypropylene oxide and from about 1% to about 20% by weight of silicone. Preferably the silicone polyether copolymer comprises at least about 40%, more preferably at least about 50%, most preferably at least about 60% by weight of polypropylene oxide. In addition, the silicone polyether copolymer preferably comprises at least about 10%, more preferably from at least about 15%, most preferably from about 15% to 30% by weight of polyethylene oxide. Furthermore, the silicone polyether block copolymer comprises from 1% to 20%, preferably 10% to 20%, more preferably about 15% by weight of silicone.

Whilst silicone polyether block copolymers are known in the art to provide a number of benefits such as foaming, defoaming, wetting, deaeration and lubricity, it has been now surprisingly found that the selection of silicone block copolymers having from 20% to 90% by weight of polypropylene oxide and from 1% to 50% of polyethylene oxide unexpectedly provide improved lubrication whilst ensuring the required level of water dispersion and or solubility verses silicone polyether block copolymers having less or no polypropylene oxide and more polyethylene oxide. Moreover, the use of such silicone block copolymers provides improved adhesion to the skin verses alternative materials such as copolymers of polyethylene oxide and polypropylene oxide. Furthermore, the inclusion of 1% to 20% of silicone by weight of the silicone polyether block copolymer surprisingly provides desirable levels of lubrication despite being present at low levels in the polymer.

The copolymers are block copolymers and may have a pendant graft structure or a linear structure. The silicone polyether block copolymer comprises from 1% to 50%, preferably from 10% to 20%, more preferably about 20% by weight of polyethylene oxide. The silicone polyether block copolymer comprises from 20% to 90%, preferably from 40% to 90%, more preferably from 50% to 80%, most preferably about 65% by weight of polypropylene oxide. The silicone polyether block copolymer comprises from 1% to 20%, preferably 10% to 20%, more preferably about 15% by weight of silicone.

The silicone polyether block copolymer preferably has a ratio of polyethylene oxide units to polypropylene oxide units of from 3.0 to 0.1, preferably from 0.6 to 0.25. The silicone polyether block copolymer preferably has a ratio of polyethylene oxide units to polypropylene oxide units to silicone units of from 20:65:15.

The silicone polyether copolymer may have a molecular weight of from about 10000 to about 19000, more preferably from about 10000 to 15000.

Suitable silicone polyether copolymers are available from Momentive under the Silwets trademark products including L7210. Preferably the silicone polyether block copolymer is liquid at 25° C., so that it can be provided in a liquid form for spray coating manufacturing methods. The melting point is determined according to ASTM D5440-93.

In one embodiment the lubricating member comprises silicone polyether block copolymer and a water soluble polymer, preferably polyethylene oxide at a weight ratio of from 1:5 to 5:1, preferably from 1:3 to 3:1 and more preferably from 1:2 to 2:1.

Optional Hydrophobic Compound

According to the invention the lubricating member may further comprise a hydrophobic compound or mixtures thereof. In one embodiment the lubricating member comprises from 1% to 40%, preferably from 5% to 40%, more preferably from about 10% to about 40%, even preferably from about 12% to about 30% by weight of a hydrophobic compound and or mixtures thereof. Suitable hydrophobic compounds include natural oils and or waxes and or fats; synthetic waxes or oils; triglycerides; skin active agents, sensates, fragrance oils, silicones and mixtures thereof. The hydrophobic material can provide a number of in use benefits such as lubrication, skin feel and cooling sensation.

The hydrophobic compound may comprise skin active agents such as, but not limited to oil soluble vitamins, such as vitamin E derivatives, including vitamin E acetate and tocopherol nicotinate; oil-soluble vitamin A derivatives, such as retinyl palmitate; lanolin; ceramides; sterols and sterol esters; salicylic acid; camphor; eucalyptol; essential oils; peppermint oil, Iso E Super [(1-(1,2,3,4,5,6,7,8-octahydro-2,3,8,8-tetramethyl-2-naphthalenyl)ethanone]; and mixtures thereof.

In some embodiments, the hydrophobic compound comprises one or more sensates. A large number of coolant compounds of natural or synthetic origin are known. The most well know is peppermint oil. Among synthetic coolants, many are derivatives of or are structurally related to menthol, i.e., containing the cyclohexane moiety, and derivatized with functional groups including carboxamide, ketal, ester, ether and alcohol. Non-limiting examples include methyl emthylamido oxalate, (under the tradename Frescolat X-cool available from Symrise), menthyl lactate (such as Frescolate ML Natural available from Symrise), and Menthyl Pyrrolidone Carboxylate also known as Menthyl PCA (under the tradename Questices available from Givaudan).

Hydrophobic compounds may be selected from capric and or caprylic triglycerides, grape seed oil, olive oil, microcrystalline wax, shea butter, cocoa butter, lanolin, essential oil, peppermint oil, isohexadecane, petrolatum, silicone polymers including waxes and oils (selected from dimethicones, phenylated silicones and mixtures thereof) and mixtures thereof.

Further Optional Lubricating Ingredients

The lubricating material may further comprise a copolymer of polyethylene oxide (PEO) and polypropylene oxide (PPO). The PEO/PPO copolymer is typically present at an amount of from 0.01% to 50%, preferably from 0.01% to 50%, more preferably from 2% to 40%, even more preferably from 3% to 25%, even more preferably still from 4% to 20% and most preferably from 5% to 10% by weight of the lubricating material or by weight of the lubricating member.

The PEO/PPO copolymer may have an average molecular weight of at least 5,000, preferably in the range of from 10,000 to 20,000, more preferably from 11,000 to 15,000, even more preferably from 12,000 to 13,000 and even more preferably still from 12,250 to 12,750. Without wishing to be bound by theory, the inclusion of a PEO/PPO copolymer of sufficient molecular weight is thought to further improve the lubrication properties of the lubricating member in aqueous conditions, especially in combination with a further water soluble polymer (particularly polyethylene oxide), and thus prevent an undesirable feeling in use.

The PEO/PPO copolymer may advantageously be a block copolymer, preferably a tri-block copolymer having the sequence: PEO-PPO-PEO, the later commercially available under tradenames such as Pluracare from BASF and Pluronic from Sigma-Aldrich.

The PEO/PPO copolymer may have a weight ratio of PEO to PPO (i.e. of ethylene oxide repeat units to propylene oxide repeat units), of from 1000:1 to 1:1000 or from 100:1 to 1:100.

Optional Hydrophobic Binders

The lubricating member may also further comprise a water-insoluble material such as hydrophobic binders. Such components may enhance the life of the lubricating material by reducing its tendency to be mechanically eroded. Advantageously, the hydrophobic binder is solid at standard temperature and pressure. Suitable hydrophobic binders include divalent metal cation stearate, preferably magnesium stearate, calcium stearate, zinc stearate, or mixtures thereof, more preferably magnesium separate; ethyl cellulose; polycaprolactone; polyethylene; polypropylene; polystyrene; butadiene-styrene copolymer (e.g. medium and high impact polystyrene); polyacetal; acrylonitrilebutadiene-styrene copolymer; ethylene vinyl acetate copolymer and blends such as polypropylene/polystyrene blend; and mixtures thereof. Preferred water insoluble materials are polyethylene, polypropylene, polystyrene; butadiene-styrene copolymer including medium and high impact polystyrene, polyacetal, acrylonitrilebutadiene-styrene copolymer, ethylene vinyl acetate copolymer (EVA) and mixtures thereof. The lubricating material may comprise from about 1 to about 50%, preferably from about 10% to about 40% more preferably from about 20% to about 40% by weight of hydrophobic binder. The hydrophobic binder may fall under the definition of hydrophobic compound as used herein and in such a case should be included for purposes of determining the amount by weight of the hydrophobic compound or mixture.

The hydrophobic binder material can be at a level of from about 22% to about 40%, preferably about 26% to about 40%, of EVA by weight of the lubricating member. The amount of EVA can also be selected at a level of from about 25% to about 32%, or from about 26% to about 30%. In one embodiment, the EVA is selected to have a % vinyl acetate (% VA) of about 18% or less, possibly less than about 18%, including less than about 12%. In one embodiment the % vinyl acetate can be, as low as about 2% to about 5%, preferably from about 2.5% to 4%. The % vinyl acetate can also be selected at a level of from about 8% to about 15%, or from about 10% to about 13%. "About" as used herein with regards to EVA level and % vinyl acetate can mean±0.1%.

In one embodiment, the lubricating member comprises ethylene vinyl acetate having a vinyl acetate % of about 18% or less. In one embodiment, the lubricating member has a total vinyl acetate level of from about 0.2% up to 7.5%, by weight of the lubricating member, preferably from about 0.4% to about 5.75%. In one embodiment the lubricating member comprises about 50% to about 78% of a water-soluble polymer; and about 20% to about 40% of ethylene vinyl acetate by weight of the lubricating member, preferably from about 26% to about 32%, said ethylene vinyl acetate having a vinyl acetate % of less than 18%. These and other types of EVA which are suitable for use in the present invention are described in U.S. Patent Publication No. 2016//0143836 and U.S. 2018/0133139.

In some embodiments, the lubricating material may comprise any other ingredients commonly found in commercially available shaving aid members. The lubricating member may therefore contain other conventional shaving aid ingredients, such as low molecular weight water-soluble release enhancing agents such as polyethylene glycol (MW<10,000, e.g., 1-10% by weight PEG-100), water-swellable release enhancing agents such as cross-linked polyacrylics (e.g., 2-7% by weight), colorants, skin feel/care actives such as water soluble cationic polymers, surfactants, soaps (including interrupted soaps), antioxidants, preservatives, emollients, beard softeners, astringents, medicinal agents, plasticizers, additional lubricants, depilatories/keratolytic materials, tackifiers, skin-soothing agents, fragrances, compatibilisers, anti-inflammatory agents, antipruritic/counterirritant materials etc. and mixture thereof. These ingredients may fall under the definition of hydrophobic compounds as used herein and should be included as such in determining the amount of hydrophobic compounds.

Method of Manufacture/Processing

The lubricating member may be formed using any method known in the art such injection molding, pressing, impregnation, spray-coating, calendaring and extrusion, molding and casting. All of the components of the lubricating member can be blended prior to molding or extrusion. For best results, it is preferred that the components are dry.

In an embodiment with a lipid phase, such as described in the summary, the CMC can be mixed into the hot molten hydrophobic phase. Dispersed within the hydrophobic phase can be the discreet particles of CMC. This mixture is then cooled and cast or set into a housing (either directly onto the razor or a separate container).

In summary, the method comprises the steps of providing a feed comprising a PEO and CMC, and molding, pressing, impregnating, spray-coating, calendaring and/or extruding said feed to form a solid lubricating member. Additional optional steps may be included depending on the process of manufacture which is utilized for example heating said feed to a temperature of from about 120° C. to about 200° C.

For example, the blended components may be extruded through a Haake System 90, ¾ inch diameter extruder with a barrel pressure of about 1000-2000 psi, a rotor speed of about 10 to 50 rpm, and a temperature of about 150°–185° C. and a die temperature of about 170°–185° C. Alternatively, a 1¼ inch single screw extruder may be employed with a processing temperature of 175°–200° C., preferably 185°–190° C., a screw speed of 20 to 50 rpm, preferably 25 to 35 rpm, and an extrusion pressure of 1800 to 5000 psi, preferably 2000 to 3500 psi. The extruded member is air cooled to about 25° C. To injection mold the lubricating member it is preferred to first extrude the powder blend into pellets. This can be done on a 1¼ or 1½ inch single screw extruder at a temperature of 120°–180° C., preferably 140°–150° C., with a screw speed of 20 to 100 rpm, preferably 45 to 70 rpm. The pellets are then molded in either a single material molding or multi-material molding machine, which may be single cavity or multi-cavity, optionally equipped with a hot-runner system. The process temperature can be from 165° to 250° C., preferably from 180° to 225° C. The injection pressure should be sufficient to fill the part completely without flashing. Depending on the cavity size, configuration and quantity, the injection pressure can range from 300 to 2500 psi. The cycle time is dependent on the same parameters and can range from 3 to 30 seconds, with the optimum generally being about 6 to 15 seconds.

The lubricating member may be manufactured using a hot melt process. In such processes the waxes are melted in a water bath to a temperature of 85° C. stirred until completely melted. The liquid silicone polyether block copolymer is then added and stirred. The temperature is then reduced to about 55° C. when the remaining components are added whilst stirring. The molten material is then poured into a mold and pressure applied. The member is removed from the mold upon cooling.

In another embodiment, the lubricating member may alternatively be provided in the form of a compressed powder. For such embodiments, the lubricating member may be manufactured whereby the water soluble polymer and other solid dry components are provided as particulates and mixed. The particulate material(s) is solid at 25° C. and preferably has a melting point of 30° C. or more. The lubricating member thus may comprise from 10% to 90% by weight of a particulate material(s) of a water-soluble polymer or mixtures thereof. A liquid component of the feed can also be spray coated onto the powders before compression.

The term compression and or compression molding or compression compaction as used herein refers to a process by which the bulk density of a particulate or powder is reduced to form a solid tablet by the application of pressure. Typically, this is performed without the application of external shear force or heat. Preferably the compression compaction is conducted below the melting point of at least one, preferably all the particulate components, preferably at ambient temperature of 25° C. As such the particulates retain their integrity after the compression process and are typically visible by the naked eye after the compression process is completed.

In certain embodiments, additional energy sources such as heat may be applied during or post compression to increase inter-particulate bonding and increase the rigidity of the resulting lubricating member, but which preferably does not result in any substantial melting of the particulate material. Preferably however this method does not require an extrusion or injection molding step or the application of energy sources such as heat.

The lubricating member may be provided in the form of a compressed powder from particulates. Preferably the particulates have an average particle size distribution of from about 50 to 1250 microns and preferably from about 300 to 1250 microns, more preferably about 1000 microns. Alternatively the particulate size is such that 90% of particles pass through a 20 mesh screen; i.e. 90% of particles are less than 841 micron in diameter. The lubricating member is compressed preferably directly into a preform or container with a compression force of typically greater than 1 KN. This may be achieved using any method and equipment known in the art in the art such as a die press. The bulk density of the particulate material prior to compression is typically about 300 to 600 kg/m$^3$ and increases to about 1000 to 1200 kg/m$^3$ following compression. Bulk density thus may be increased by about 200% to about 400% after the compression. Whilst no bound by theory, it has been found that the use of particulate compression manufacturing, preferably cold particulate compression (i.e. at 25° C. or less) to form the lubricating member enables highly lubricous components to be incorporated therein whilst not negatively impacting the water solubility and swelling performance of the water soluble polymer. This also allows flexibility in the size of the resulting lubricating member to be used for multiple razor cartridges.

Hair Removal Head

According to some embodiments of the invention, the lubricating member finds particular application for hair removal devices. Hair removal devices generally comprise a hair removal head and a handle or grip portion, upon which the hair removal head is mounted. The hair removal device can be manual or power driven and can be used for wet and/or dry application. The hair removal head can include a wide scraping surface such as where the hair removal device is used with a depilatory, or be a razor cartridge or foil where the device is a shaving razor. The hair removal head may be replaceable and/or pivotally connected to a cartridge connecting structure and in turn or independently (e.g. permanently fixed) to a handle. In some embodiments, the cartridge connecting structure includes at least one arm to releasably engage the hair removal head.

The hair removal head typically comprises one or more elongated edges usually positioned between a first and second end, said one or more elongated edges comprising a tip extending towards said first end. Where the hair removal head is a razor cartridge the one or more elongated edges can include blades. For example, U.S. Pat. No. 7,168,173 generally describes a FUSION® razor that is commercially available from The Gillette Company and which includes a razor cartridge with multiple blades. Additionally, the razor cartridge may include a guard as well as a lubricating member. A variety of razor cartridges can be used in accordance with the present invention. Non limiting examples of suitable razor cartridges, with and without fins, guards, and/or shave aids, include those marketed by The Gillette Company under the FUSION®, VENUS® product lines as well as those disclosed in U.S. Pat. Nos. 7,197,825, 6,449,849, 6,442,839, 6,301,785, 6,298,558; 6,161,288, and U.S. Patent Publ. 2008/060201. Those of skill in the art will understand that the lubricating member can be used with any currently marketed system or disposable razor, including those having 2, 3, 4 or 5 blades. In such a case, the hair removal device is a razor, the hair removal head is a razor cartridge and the one or more elongated edges are blades. Another example of a hair removal device is a scraping tool for use with a hair removal composition, i.e. a depilatory.

In some embodiments, said at least one lubricating member is located on the portion of the cartridge that contacts skin during the hair removal process, forward and/or aft of the blades. A feature "forward" of the one or more elongated edges, for example, is positioned so that the surface to be treated with by the hair removal device encounters the feature before it encounters the elongated edges. A feature "aft" of the elongated edge is positioned so that the surface to be treated by the hair removal device encounters the feature after it encounters the elongated edges. Where more than one lubricating member is provided on the hair removal device, they can be the same (identical) or different, in terms of physical shape/structure and/or chemical composition, and one or more of them may comprise the spray coated particulate.

In some particular embodiments, a plurality (e.g. 2, a first and second) of lubricating members may be provided on the hair removal head, with the first lubricating member comprising the same composition or different. These lubricating members may be placed collectively (for example adjacent to one another) ahead of or behind the elongated edges (e.g. blades on a razor cartridge), including side by side, or separately with one ahead of the elongated edges and the other behind.

The lubricating member may be free standing utilizing a suitable attachment means such as adhesive or may be contained at least partially within a container.

The container typically has a base and at least one side wall extending vertically preferably perpendicular from said base and a skin contacting surface. In a preferred embodiment said container comprises a base and at least 2 side walls, more preferably at least 4 side walls, preferably said walls completely enclosing the base. Typically, each pair of walls are substantially parallel and preferably one pair of walls is substantially parallel to the at least two blades. Alternatively, the base may be enclosed by a one piece single wall. The container may form any shape including substantially rectangular, or oval. The container typically has a front wall adjacent the blades and a rear wall, preferably substantially parallel thereto and furthest from said blades.

The container is preferably further provided with at least one dispensing orifice for dispensing the lubricating member onto the skin during use. In one embodiment the container is provided with a top extending substantially perpendicular from the side wall (s). The container would in such an embodiment typically have a receiving region for receiving the lubricating member. The top may be substantially parallel to the base or it may be provided at an angle such that the distance of the top from the blade plane increases or decreases as the distance of the container from the blades increases. In one embodiment the height of the top of the container increases in distance from the blade plane as the container distance from the blades increases. In an alternative embodiment the height of the top of the container decreases in distance from the blade plane as the container distance from the blade increases.

The orifice may be of any shape and may, for example, have a cross sectional area of from about 0.00324 to about 1.613 $cm^2$. Small orifices can also be provided with cross sectional area of from about 0.0324 to about 0.324 $cm^2$, or from about 0.0645 to about 0.16135 $cm^2$. Larger orifices can have cross sectional areas of from about 0.324 to about 1.613 $cm^2$, or from about 0.645 to about 1.29 $cm^2$. The container may comprise a single orifice or multiple orifices which may be large and or small. In one embodiment the container comprises at least two orifices. Combinations of small and large orifices can also be provided on the same lubricating member, or on separate members on the same cartridge, depending on the desired dispense rate and amount of exposure of the lubricating material to water. In one embodiment the top of the container is provide with one preferably two orifices, more preferably two substantially identical orifices adjacent one another.

The lubricating surface of the container which has a surface area, while the at least one orifice (i.e. the sum for all orifices if a plurality are present) has a cross sectional area such that the surface area and cross sectional area are in a ratio of from about 50:1 to about 1:1, or about 25:1 to about 2:1, or about 10:1 to about 3:1.

In some embodiments, at least a portion of said container is not linear for example angled or curvilinear. Curvilinear as defined herein means that at least a portion is curved such that it does not form a straight line. Where at least two containers are provided, they can also be positioned relative to one another such that they do not form a straight line. Alternatively, the curved or angled nature is such that it forms at least a partial ring. A partial ring, as defined herein, means that the structure has at least two curved or angled sections which are concave to form an inner region. The partial ring can also include a curved or angled portion which is positioned convex to said inner region. One or more of said containers may also be positioned relative to one another to form a full ring.

The container can be formed of a variety of materials. The container may, preferably be for example, provided from a non-water soluble material such that it does not degrade or dissolve during normal use.

The container typically has sufficient mechanical strength and rigidity to provide adequate mechanical strength to the entire lubricating member, both as initially produced and after a significant amount of lubricating material has leached out of the container. Alternatively or in addition a further reinforcing member may also be utilized. In some embodiments, the container comprises a base and one or more side walls, forming a receiving region, or channel, onto or into which the lubricating material is placed.

The side walls may or may not be the same height (as measured extending away from the base of the container). At least one of the side walls can have a height of about 0.1 cm to about 1 cm, preferably from about 0.2 cm to about 0.4 cm. The pair of side walls can be biased away from each other as the walls extend away from said base, or they can be biased towards each other. At least one wall extends vertically from the base and is preferably perpendicular to the blade plane (P). One or both ends of the container can be enclosed, e.g. as described in U.S. Pat. No. 7,581,318. The term maximum height of at least one wall as used herein refers to the first front wall preferably substantially parallel to the at least two blades and closest thereto or it refers to the rear wall farthest from said at least two blades. In one embodiment the said at least one wall is closest to said at least two blades. In an alternative embodiment the at least one wall is farthest from said at least two walls. In one embodiment, the ratio of the height of the front wall to the rear wall is from 5:1 to 1:5, more preferably from 2:1 to 1:2 and more preferably the height of the front wall is greater than the rear wall. The walls have a thickness of from 0.1 cm to 1.0 cm, preferably from 0.3 to 0.5 cm.

The container may be made of a water-insoluble polymer, particularly a thermoplastic resin. Thermoplastic resins are those materials which can be extruded or molded into a shape and are resilient under normal environmental conditions such as contact with water, even up to normal household hot water temperatures (for example up to 125° C.); normal wear and tear by consumers during use; device assembly and shipping, etc. Thermoplastic resins suitable for use in the carrier include polystyrene, high impact polystyrene (polystyrene-butadiene), polypropylene, filled polypropylene, polyethylene, nylon ethylene vinyl acetate, and blends such as 70% nylon/30% polyethylene oxide, 60% polystyrene/40% polyethylene oxide butadiene styrene copolymer, polyacetal, acrylonitrile-butadiene styrene copolymer, and mixtures thereof. The preferred resins are high impact polystyrene, polystyrene, ethylene vinyl acetate (EVA), and mixtures thereof.

In some embodiments, the cartridge comprises a guard comprising at least one elongated flexible protrusion to engage a user's skin. The at least one flexible protrusion may comprise flexible fins generally parallel to said one or more elongated edges. Said at least one flexible protrusion may additionally or alternatively comprise flexible fins comprising at least one portion which is not generally parallel to said one or more elongated edges. Non-limiting examples of suitable guards include those used in current razor blades and include those disclosed in U.S. Pat. Nos. 7,607,230 and 7,024,776; (disclosing elastomeric/flexible fin bars); 2008/0034590 (disclosing curved guard fins); 2009/0049695A1 (disclosing an elastomeric guard having guard forming at least one passage extending between an upper surface and a lower surface). In some embodiments, said lubricating member is positioned on the cartridge aft of the guard and forward of said elongated edge. In another embodiment, the lubricating member is positioned on the cartridge forward of the guard. This embodiment can be particularly useful to deliver the lubricating member prior to contact with the guard.

I. FORMULATION EXAMPLES

| Ingredient | Example 1 (% w/w) | Example 2 (% w/w) | Example 3 (% w/w) | Example 4 (% w/w) |
|---|---|---|---|---|
| Polyox WSR coag | — | 10 | — | 20 |
| Polyox N60k | — | — | — | — |
| Silwet L7210 * | — | — | 20 | 40 |
| Cekol 50,000 (CMC) | 30 | — | 30 | 10 |
| Cekol 30,000 (CMC) | — | 20 | — | — |
| Petrolatum | 40 | 35 | 20 | — |
| Cetyl alcohol | 30 | 30 | 25 | — |
| Stearyl alcohol | — | — | — | 30 |
| Lauric acid | — | 5 | 5 | — |
| Total | 100 | 100 | 100 | 100 |

Suppliers:
* Momentive,
** Dow Chemicals,
*** Ashland,
$ Dow Corning,
Sonnenborn Formulation Examples 1-4 are Prepared as Follows 1. Sanitize all equipment
2. Turn on water bath/vessel jacket to 75° C.
3. Add lipophilic structurants (cetyl or stearyl alcohol, lauric acid) and stir with overhead stirrer until completely melted
4. Add oil phase ingredients (Silwet, petrolatum) and mix until fully liquid
5. Reduce heat to 60° C. and add powder ingredients (Polyox, Cekol) until fully dispersed.
6. Pour mixture into a mould or container
7. Assemble part onto razor cartridge.

| Material | Example 5 (%) |
|---|---|
| Elvax 750 * | 31.00% |
| Carbowax 4600 PEG ** | 5.00% |
| PCL CAPA 6506 *** | 5.00% |
| Cekol 50,000 | 10.00% |
| Irganox 1010 | 0.50% |
| PEO N750 ** | 19.40% |
| PEO 308 ** | 29.10% |

Suppliers:
* Dupont,
** Dow Chemicals,
*** Perstorp

Formulation Example 5 is Prepared as Follows

Lubricating member of the present invention is made by extrusion or another high temperature processing, such as injection molding, compression molding, compacting, ultrasonic or radio frequency sintering, and slot coating. High temperature processing degrades/decomposes the water soluble polymers (PEO) as well as the additional benefit ingredients. In one embodiment with EVA grade Elvax 660 (purchased from Dupont) in the lubricating member, the extrusion process temperature is lowered to 110° C. In one embodiment, the lubricating member comprising the thermally resilient skin care active can further be coated or layered with another lubricating member. In one embodiment, all of the components of the strip, including the high mol. wt. PEO and low mol. wt. PEO mixture can be blended alone or in combination with other ingredients prior to molding or extrusion. It can be preferred that the components are free flowing powders, however, liquid skin actives may be adsorbed onto one or more of the other components in the strip that are in powder form.

The PEO feed can be combined with a second feed if additional ingredients are desired. The feed or feeds can be mixed and processed through a step of extrusion through a die to form a lubricating member suitable for use as a lubricating member. As will be explained below, said step of extruding can include subjecting said mixture to a pressure of from about 1000 psi to about 7500 psi and/or a temperature of from about 100° C. to about 160° C.

The blended components may be extruded through a Rondol 18, 18 mm diameter extruder with a barrel pressure of about 500-1000 psi, a rotor speed of about 10 to 50 rpm, and a temperature of about 100°-160° C. and a die temperature of about 100°-160° C. Alternatively, a 1½ inch single screw extruder may be employed with a processing temperature of 100°-160° C., preferably 110-130° C., a screw speed of 20 to 50 rpm, preferably 25 to 50 rpm, and an extrusion pressure of 1800 to 7500 psi, preferably 4000 to 6500 psi. Other extrusion conditions can also be employed. The extruded strip is cooled to about 25° C. To injection mold the strips it is preferred to first extrude the powder blend into pellets. This can be done on a 1¼ or 1½ inch single screw extruder at a temperature of 100°-140° C., preferably 110°-130° C., with a screw speed of 20 to 100 rpm, preferably 45 to 70 rpm. The pellets are then molded in either a single material molding or multi-material molding machine, which may be single cavity or multi-cavity, optionally equipped with a hot-runner system. The process temperature can be from 100° to 185° C., preferably from 110° to 145° C. The injection pressure should be sufficient to fill the part completely without flashing. Depending on the cavity size, configuration and quantity, the injection pressure can range from 300 to 2500 psi. The cycle time is dependent on the same parameters and can range from 3 to 30 seconds, with the optimum generally being about 6 to 15 seconds. In one embodiment, one or more feeds can be preheated or they can be fed in at ambient temperature.

In one embodiment, the process further comprises a step of providing a lubricating member receiving region (such as a portion of a first layer or base or sheath) and distributing a volume of the PEO feed into said lubricating member receiving region (to form a second layer or core). Where a sheath and core system are used, the sheath can be performed by molding and the core can be thereafter formed within the sheath by providing said PEO mixture in a fluid or flowable form (such as a liquid or powder) then solidifying it such as by pressurizing, heating and or ultrasonically compressing said PEO feed within said lubricating member receiving region. Non-limiting examples of ways to form such lubricating members are disclosed in U.S. Pat. No. 6,298,558 or 7,581,318 as well as WO 2011/047221.

|  | Example 6 (% w/w) | Example 7 (% w/w) |
|---|---|---|
| Polyox WSRcoag | 90.0 | — |
| Polyox N60k | — | 88.0 |
| Silwet L7210 | — | 2.0 |
| Cekol 50,000 | 10.0 | 10.0 |
| Total | 100 | 100 |

Formulation Examples 6-7 are Prepared as Follows

The lubricating materials (PEO, Cekol) in the table above are made by dry mixing the ingredients in the examples and spray coating the silwet onto the powder blend if used. An appropriate amount of the resulting mix is then compressed and compacted into the lubricating member container using a die press at 2.2 KN for about 5 seconds.

As used herein, molecular weights (mol·wt·s) are provided in unified atomic mass units, daltons, or g/mol. It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein. Similarly, it should be understood that each feature of the each specified embodiment of the invention may be independently applied to each other specified embodiment, as if all such combinations were expressly written herein, unless these combinations are specifically excluded or the relevant features are innately incompatible (e.g. the features are directly contradictory).

All parts, ratios, and percentages herein, in the Description, Examples, and Claims, are by weight of the lubricating member and all numerical limits are used with the normal degree of accuracy afforded by the art, unless otherwise specified.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

What is claimed is:

1. A razor comprising:
  a. a housing having a lubricating surface;
  b. at least one blade with a blade tip, wherein said blade tip is exposed on said lubricating surface of the housing;
  c. a lubricating member position on the lubricating surface of said housing, said lubricating member comprising a lubricating material comprising a mixture of a polyethylene oxide and a carboxymethyl cellulose, wherein said carboxymethyl cellulose forms at least one discreet particle of at least 95% carboxymethyl cellulose and the ratio of carboxymethyl cellulose to polyethylene oxide is in the range of 65:35 to 55:45.

2. The razor of claim 1, wherein said discreet particle has a particle diameter less than 600 microns.

3. The razor of claim 1, wherein at least 50% of said carboxymethyl cellulose forms a plurality of carboxymethyl cellulose particles within said lubricating member.

4. The razor of claim 3, wherein said plurality of carboxymethyl cellulose particles has an average particle size of less than about 600 microns.

5. The razor of claim 1, wherein said carboxymethyl cellulose has an average molecular weight over 30,000 Daltons.

6. The razor of claim 1, wherein said the carboxymethyl cellulose has a formulas of:

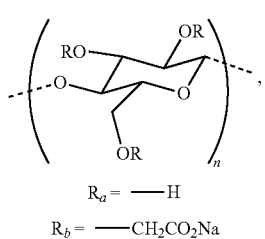

$R_a = \text{---} H$
$R_b = \text{---} CH_2CO_2Na$ wherein the cellulose has 3 R groups per repeating unit, said R groups selected from Ra or Rb.

7. The razor of claim 6, wherein the carbomethyl cellulose has an average degree of hydrophobic moiety substitution is in the range of from 0.001 to 0.2.

8. The razor of claim 6, wherein said carboxymethyl cellulose has a degree of carbomethyl substitution from about 0.75 to about 0.95.

9. The razor of claim 1, wherein said carboxymethyl cellulose is derived from wood.

10. The razor of claim 1, wherein said polyethylene oxide has an average molecular weight from 3 MM daltons to 5 MM daltons.

11. The razor of claim 10, wherein said lubricating member comprises a mixture of more than one polyethylene oxide.

12. The razor of claim 1, wherein said lubricating member further comprises a lipid phase, said lipid phase comprising:
   a. from about 10% to about 70% by weight of the lubricating member of a lipophilic structurant;
   b. from about 10% to about 70% a liquid phase comprises a silicone polyether block copolymer comprising a mixture of polyethyelene oxide, polyproylene oxide, and silicone.

13. The razor of claim 12, wherein said lipophilic structurant is selected from the group consisting of:
   a. cetyl alcohol, stearyl alcohol, or mixture thereof, and
   b. a microcrystalline wax.

14. The razor of claim 12, where said silicone polyether block polymer has a ratio of polyethylene oxide units to polypropylene oxide units to silicone units of 20:65:15, and a molecular weight of from about 10000 to about 19000.

15. A hair removal device comprising:
   a. a housing having a lubricating surface;
   b. a lubricating member position on the lubricating surface of said housing, said lubricating member comprising:
      i. from about 10% to about 70% of a polyethylene oxide;
      ii. from about 10% to about 70% of a carboxymethyl cellulose,
   c. wherein said carboxymethyl cellulose forms at least one discreet particle of at least 95% carboxymethyl cellulose,
   d. wherein the carboxymethyl cellulose has a formulas of:

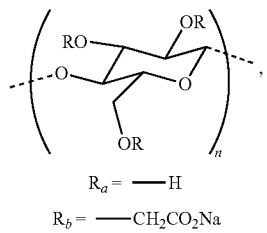

$R_a = \text{---} H$
$R_b = \text{---} CH_2CO_2Na$ wherein the cellulose has 3 R groups per repeating unit, said R groups selected from Ra or Rb,
wherein said carboxymethyl cellulose has a degree of carbomethyl substitution from about 0.75 to about 0.95.

16. The hair removal device of claim 15, wherein said lubricating member further comprises a lipid phase, said lipid phase comprising:
   a. from about 10% to about 70% by weight of the lubricating member of a lipophilic structurant, wherein said lipophilic structurant is selected from the group consisting of:
      i. cetyl alcohol, stearyl alcohol, or mixture thereof, and
      ii. a microcrystalline wax;
   b. from about 10% to about 70% a liquid phase comprises a silicone polyether block copolymer comprising a mixture of polyethyelene oxide, polyproylene oxide, and silicone;
   c. and wherein the level of polyethylene oxide is from 10% to about 30%, and the level of carboxymethyl cellulose is from about 20% to about 30%.

17. The hair removal device of claim 15, further comprising a ratio of carboxymethyl cellulose to water soluble polymer in the range of 1:1 to about 7:3.

18. The hair removal device of claim 15, further comprising from about 10% to about 40% of a water insoluble material selected from the group consisting of:
polyethylene, polypropylene, polystyrene; butadiene-styrene copolymer including medium and high impact polystyrene, polyacetal, acrylonitrilebutadiene-styrene copolymer, ethylene vinyl acetate copolymer and mixtures thereof.

19. A method of forming a lubricating member for use on a hair removal device, the method comprising:
   a. providing a polyethylene oxide;
   b. providing a carboxymethyl cellulose in a solid form;
   c. contacting said polyethylene oxide with said carboxymethyl cellulose to form a mixture;
   d. forming a lubricating member from said mixture, wherein said carboxymethyl cellulose forms a discreet particle of at least 95% carboxymethyl cellulose within said lubricating member.

* * * * *